US009719920B2

(12) United States Patent
Grunzweig et al.

(10) Patent No.: US 9,719,920 B2
(45) Date of Patent: Aug. 1, 2017

(54) SCATTEROMETRY SYSTEM AND METHOD FOR GENERATING NON-OVERLAPPING AND NON-TRUNCATED DIFFRACTION IMAGES

(71) Applicant: KLA-Tencor Corporation, Milpitas, CA (US)

(72) Inventors: Tzahi Grunzweig, Timrat (IL); Andrew Hill, Berkeley, CA (US); Barry Loevsky, Yokneam Ilit (IL)

(73) Assignee: KLA-Tencor Corporation, Milpitas, CA (US)

( * ) Notice: Subject to any disclaimer, the term of this patent is extended or adjusted under 35 U.S.C. 154(b) by 42 days.

(21) Appl. No.: 14/497,439

(22) Filed: Sep. 26, 2014

(65) Prior Publication Data

US 2015/0022822 A1 Jan. 22, 2015

Related U.S. Application Data

(63) Continuation of application No. PCT/US2014/046724, filed on Jul. 15, 2014.

(60) Provisional application No. 61/847,883, filed on Jul. 18, 2013.

(51) Int. Cl.
  *G01B 11/24* (2006.01)
  *G01N 21/47* (2006.01)
  *G03F 7/20* (2006.01)

(52) U.S. Cl.
  CPC ......... *G01N 21/4788* (2013.01); *G03F 7/701* (2013.01); *G03F 7/70633* (2013.01); *G01B 2210/48* (2013.01); *G01N 2201/06113* (2013.01)

(58) Field of Classification Search
  CPC . G03F 7/701; G03F 7/70633; G01N 21/8806; G01N 2201/06; G01N 21/4788; G01N 2201/06113; G01B 2210/48
  USPC ......................................................... 356/601
  See application file for complete search history.

(56) References Cited

U.S. PATENT DOCUMENTS

| | | | | |
|---|---|---|---|---|
| 5,237,435 A | * | 8/1993 | Kurematsu | G02F 1/1333 348/751 |
| 5,638,211 A | * | 6/1997 | Shiraishi | 359/559 |
| 5,859,424 A | | 1/1999 | Norton et al. | |
| 7,573,584 B2 | | 8/2009 | Den Boef et al. | |

(Continued)

FOREIGN PATENT DOCUMENTS

KR 1020080027748 A 3/2008

*Primary Examiner* — Hina F Ayub
(74) *Attorney, Agent, or Firm* — Suiter Swantz pc llo

(57) ABSTRACT

Scatterometry measurement systems, illumination configurations and respective methods are provided, which comprise illumination beams that have vertical projections on a target plane comprising both a parallel component and a perpendicular component, with respect to a target measurement direction. The illumination beams propagate at an angle to the plane defined by the measurement direction and a normal to the targets surface and generate diffraction images which are off-center at the imaging pupil plane. The eccentric diffraction images are spatially arranged to avoid overlaps and to correspond to measurement requirements such as spot sizes, number of required diffraction orders and so forth. The illumination beams may be implemented using illumination pupil masks, which provide a simple way to increase scatterometry measurements throughput.

36 Claims, 15 Drawing Sheets

(56) References Cited

U.S. PATENT DOCUMENTS

| | | | |
|---|---|---|---|
| 2003/0206298 A1* | 11/2003 | Bischoff | G03F 7/70633 |
| | | | 356/369 |
| 2003/0210393 A1 | 11/2003 | Vaez-Iravani et al. | |
| 2005/0117221 A1* | 6/2005 | Ogawa | G02B 27/0037 |
| | | | 359/565 |
| 2006/0066855 A1* | 3/2006 | Boef | G03F 7/70341 |
| | | | 356/401 |
| 2006/0197951 A1 | 9/2006 | Frommer et al. | |
| 2007/0153273 A1* | 7/2007 | Meeks | 356/369 |
| 2007/0229807 A1* | 10/2007 | Lally | G01N 21/9501 |
| | | | 356/237.1 |
| 2008/0129986 A1* | 6/2008 | Walsh | G01B 11/24 |
| | | | 356/138 |
| 2010/0201963 A1* | 8/2010 | Cramer et al. | 355/67 |
| 2011/0102753 A1* | 5/2011 | Van De Kerkhof | G01N 21/4788 |
| | | | 355/27 |
| 2012/0123581 A1* | 5/2012 | Smilde et al. | 700/105 |
| 2013/0077086 A1 | 3/2013 | Chuang et al. | |
| 2013/0141730 A1* | 6/2013 | Quintanilha | 356/446 |
| 2014/0146322 A1* | 5/2014 | Hill et al. | 356/446 |

* cited by examiner

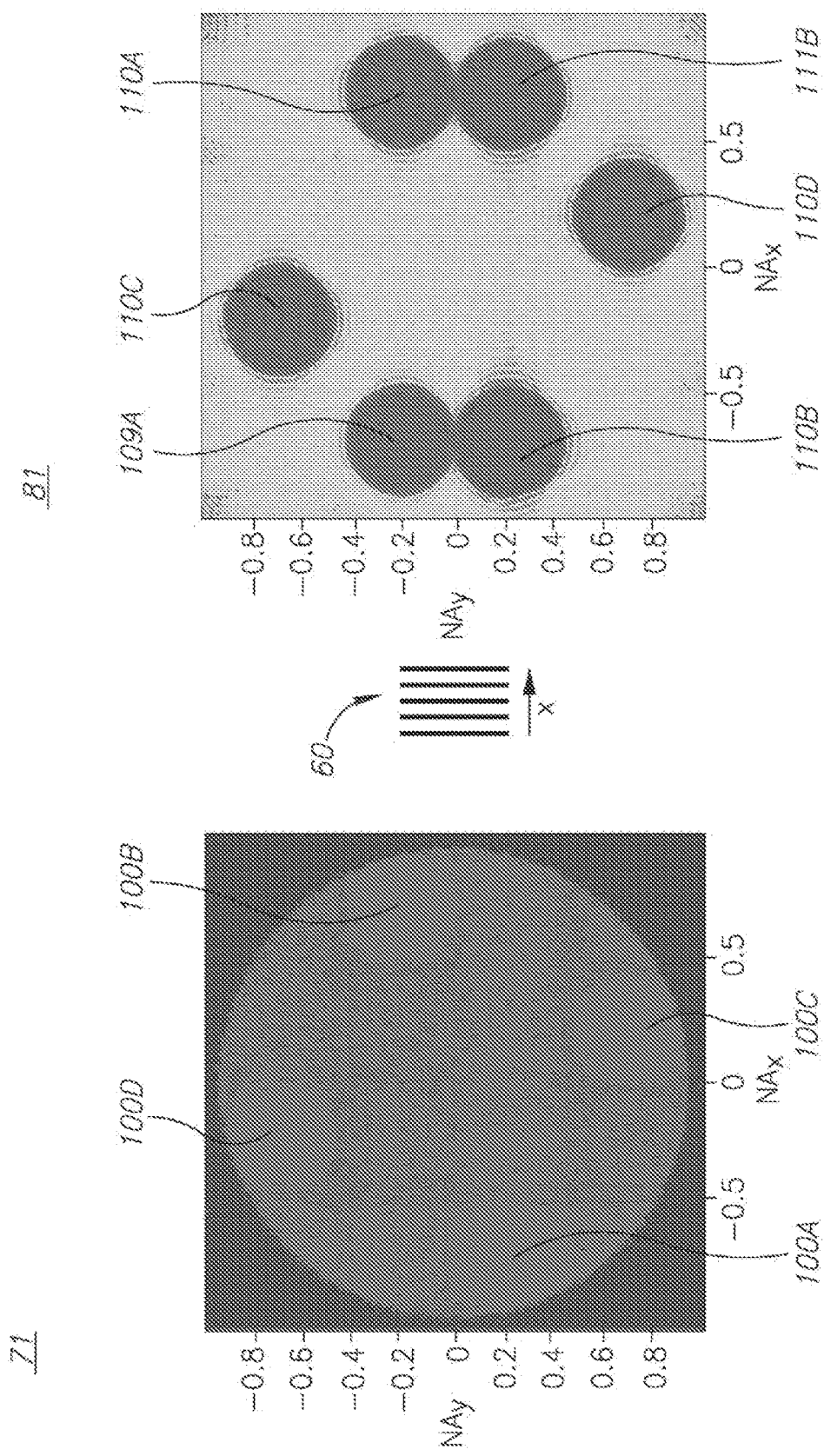

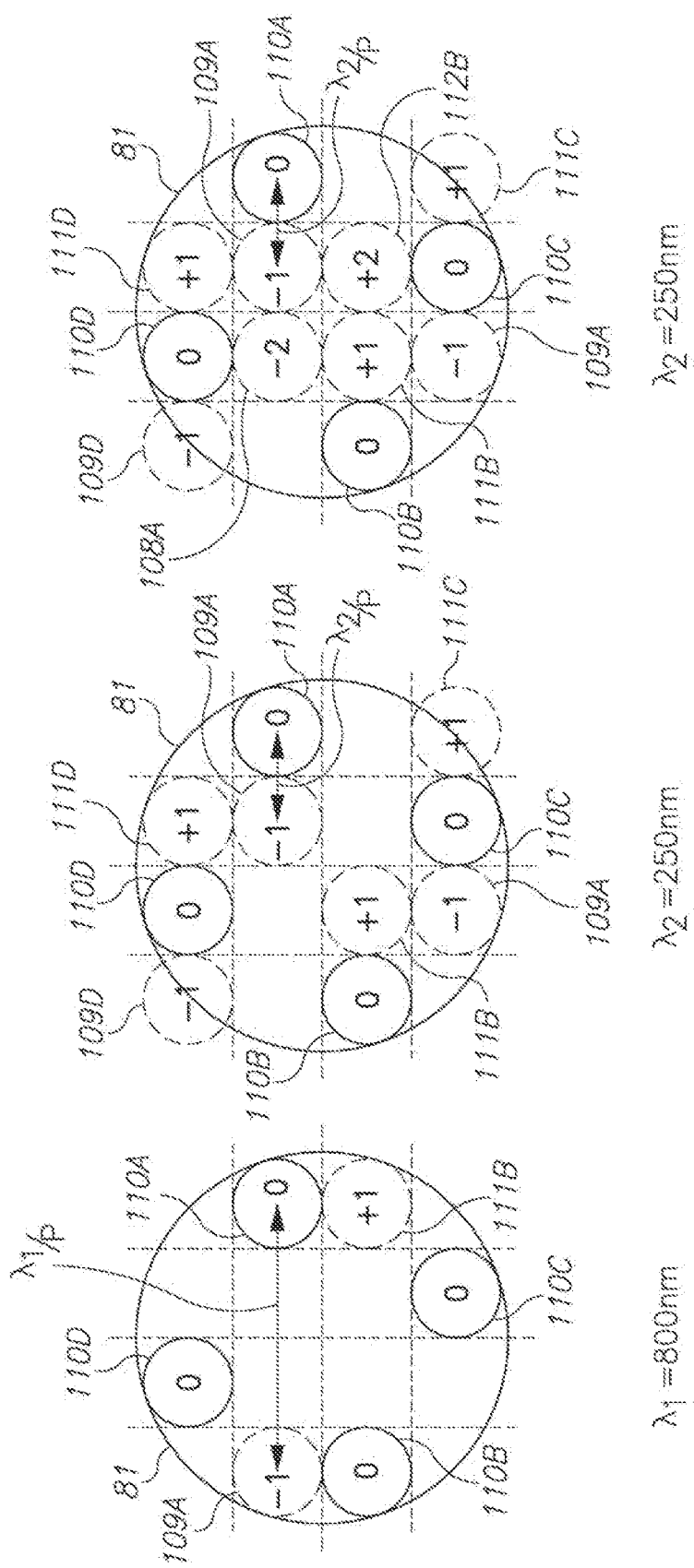

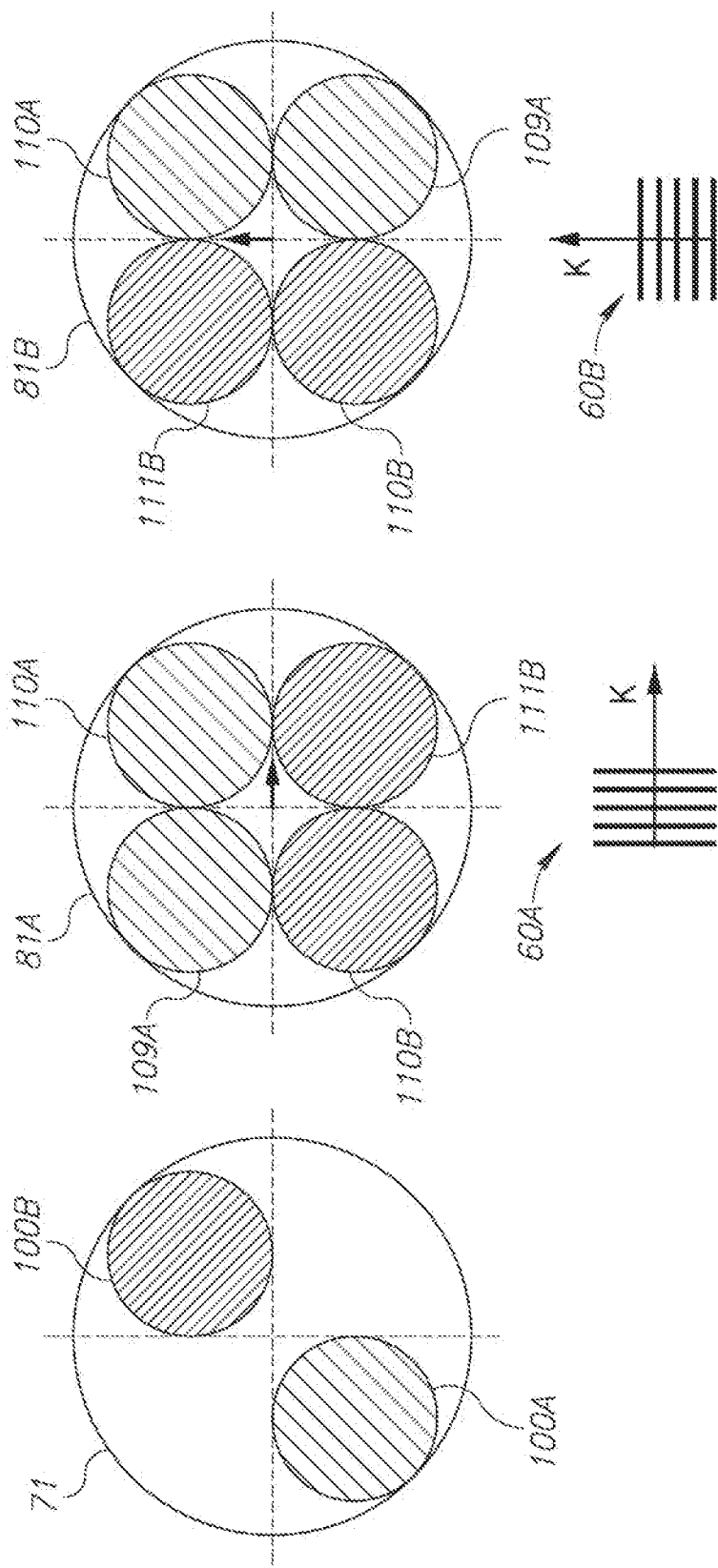

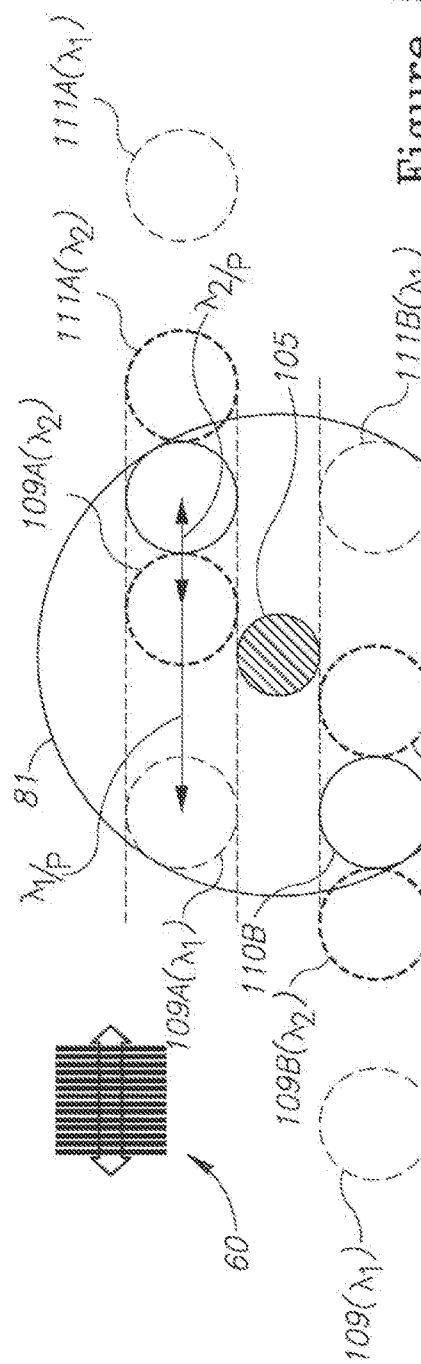
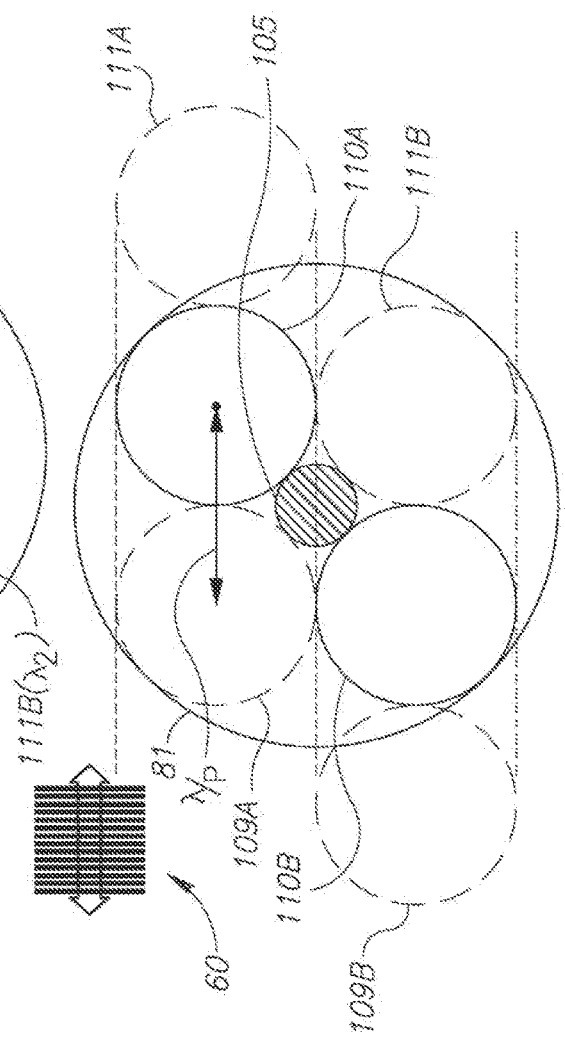
Figure 8A
Figure 8B

200

210 — ILLUMINATING A SCATTEROMETRY TARGET WITH ILLUMINATION BEAM(S) HAVING BOTH PARALLEL AND PERPENDICULAR COMPONENTS OF THEIR VERTICAL PROJECTION ON THE TARGET PLANE

212 — CONFIGURING THE ILLUMINATION PROPAGATION DIRECTION TO BE OUT OF A PLANE DEFINED BY THE TARGET'S MEASUREMENT DIRECTION AND A NORMAL TO THE TARGET

220 — ILLUMINATING THE TARGET WITH ONE OR MORE PAIRS OF OPPOSITE ILLUMINATION BEAMS

230 — POSITIONING THE ILLUMINATION BEAMS TO ENABLE SCATTEROMETRY MEASUREMENTS OF THE TARGET ALONG TWO MEASUREMENT DIRECTIONS

240 — POSITIONING THE ILLUMINATION BEAMS IN A PUPIL PLANE TO BE OFF A TARGET AXIS AND OFF AN AXIS PERPENDICULAR TO THE TARGET AXIS

250 — ARRANGING THE ILLUMINATION BEAM(S) AT A PERIPHERY OF THE PUPIL PLANE

Figure 12

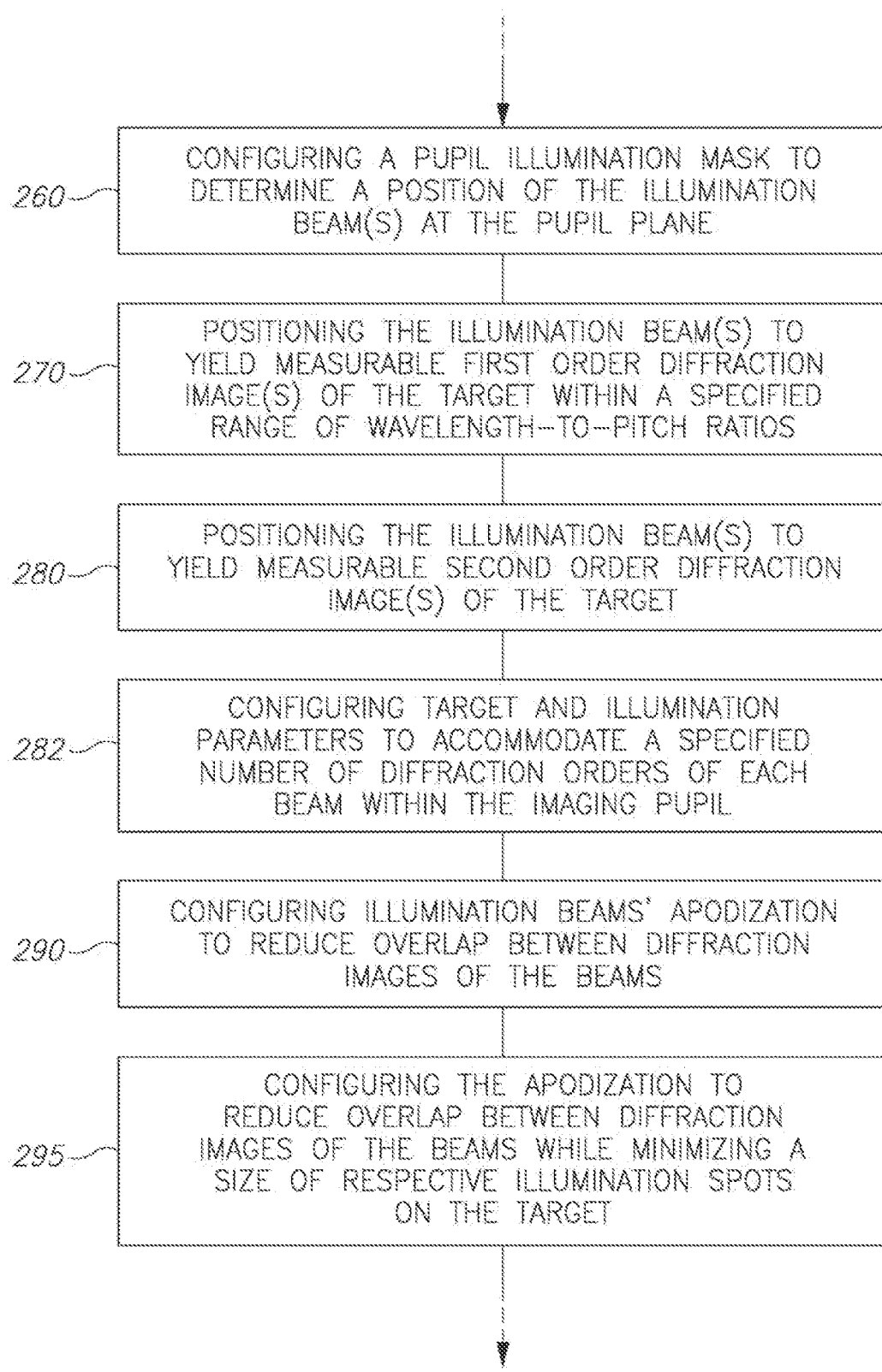
Figure 12 (cont. 1)

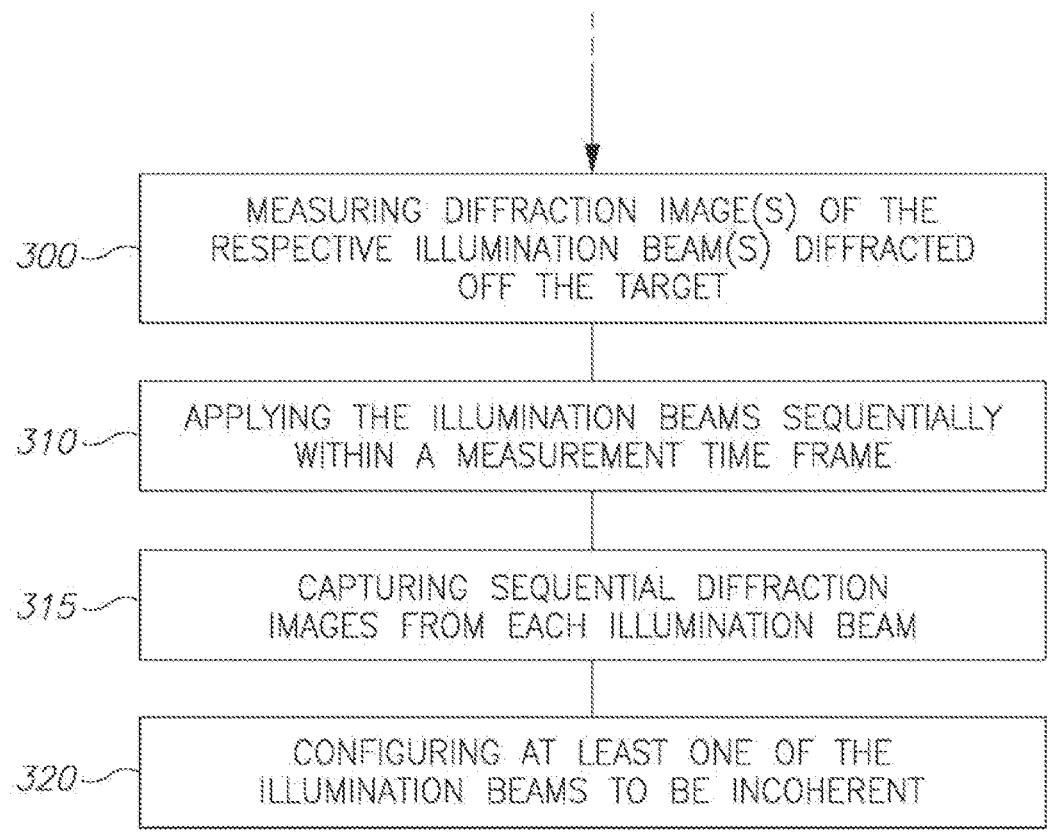
Figure 12 (cont. 2)

SCATTEROMETRY SYSTEM AND METHOD FOR GENERATING NON-OVERLAPPING AND NON-TRUNCATED DIFFRACTION IMAGES

CROSS-REFERENCE TO RELATED APPLICATIONS

This application is filed under 35 U.S.C. §111(a) and §365(c) as a continuation of International Patent Application No. PCT/US2014/046724 filed Jul. 15, 2014, which application claims the benefit of U.S. Provisional Patent Application No. 61/847,883 filed on Jul. 18, 2013, which applications are incorporated herein by reference in their entirety.

BACKGROUND OF THE INVENTION

1. Technical Field

The present invention relates to the field of metrology scatterometry measurements, and, more particularly, to illumination patterns in scatterometry.

2. Discussion of Related Art

Metrology targets are designed to enable the measurement of parameters that indicate the quality of wafer production steps and quantify the correspondence between design and implementation of structures on the wafer. Scatterometry overlay (SCOL) targets are periodic structures (e.g., gratings) which are used to produce diffraction patterns for metrology measurements. Diffraction patterns are produced by illuminating the periodic structures along their measurement direction (e.g., perpendicularly to the elements of the grating), as illustrated for example in FIG. 1 below.

FIG. 1 is a high level schematic illustration of prior art scatterometry illumination. Input pupil image 71 illustrates the illumination sources 90 (log intensity) at the periphery of the pupil plane, as they are arranged along the X and Y axes to enable diffraction measurements at directions X and Y of respective target 60 (illustrated is target 60 having a measurement direction along the X axis). Positioning illumination sources 90 along respective measurement axes and at the periphery of the pupil plane maximizes the incidence angle of the illumination upon target 60 in the plane defined by the measurement direction and the normal to the target's surface. Resulting image 81 depicted at the detector's (pupil) plane illustrates the log intensity of the resulting spots—spots 92Y of non-diffracted Y axis illumination sources 90, spots 92X which are zero order diffraction images of sources 90 along the X axis and spots 91X which are $\pm 1^{st}$ order diffraction images of sources 90 along the X axis (the exact identity of the two central spots of +1 or −1 order images of left or right X axis source 90 respectively depends on measurement configurations).

The disadvantage of the prior art quadruple illumination method is that the maximal diffraction angle is limited by the presence of the zero order diffracted light spots 92X. Conceptually, different masks could have been used to measure independently the diffraction of the different orders. Measuring both the first and minus first diffraction order simultaneously decreases total measurement time and machine complexity. However, when illuminations from both directions are present, the diffraction orders resulting from one aperture in the quadruple cannot overlap any of the orders of a second aperture. In the prior art quadruple arrangement, this is realized by limiting the diffraction angle (i.e., by using shorter wavelengths or longer pitch gratings), thus limiting the method's usefulness.

SUMMARY OF THE INVENTION

One aspect of the present invention provides a scatterometry measurement system comprising at least one illumination beam, wherein a vertical projection of the at least one illumination beam on a target plane comprises both a parallel component and a perpendicular component, with respect to a target measurement direction.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 4 is a simulated example for scatterometry measurements along the x axis according to some embodiments of the invention;

FIG. 6A is a high level schematic illustration of an illumination beam arrangement which allows scatterometry measurements at multiple wavelengths, according to an embodiment of the invention;

FIG. 6B is a high level schematic illustration of an illumination beam arrangement which allows scatterometry measurements at multiple wavelengths, according to an embodiment of the invention;

FIG. 6C is a high level schematic illustration of an illumination beam arrangement which allows scatterometry measurements at multiple wavelengths, according to an embodiment of the invention;

FIG. 7A is a high level schematic illustration of an illumination beam arrangement which optimizes scatterometry measurements at a given wavelength, according to an embodiment of the invention;

FIG. 7B is a high level schematic illustration of an illumination beam arrangement which optimizes scatterometry measurements at a given wavelength, according to an embodiment of the invention;

FIG. 7C is a high level schematic illustration of an illumination beam arrangement which optimizes scatterometry measurements at a given wavelength, according to an embodiment of the invention;

FIG. 8A is a high level schematic illustration of wavelength-adaptable illumination according to an embodiment of the invention;

FIG. 8B is a high level schematic illustration of wavelength-optimized illumination according to an embodiment of the invention;

DETAILED DESCRIPTION OF THE INVENTION

Figure 1:
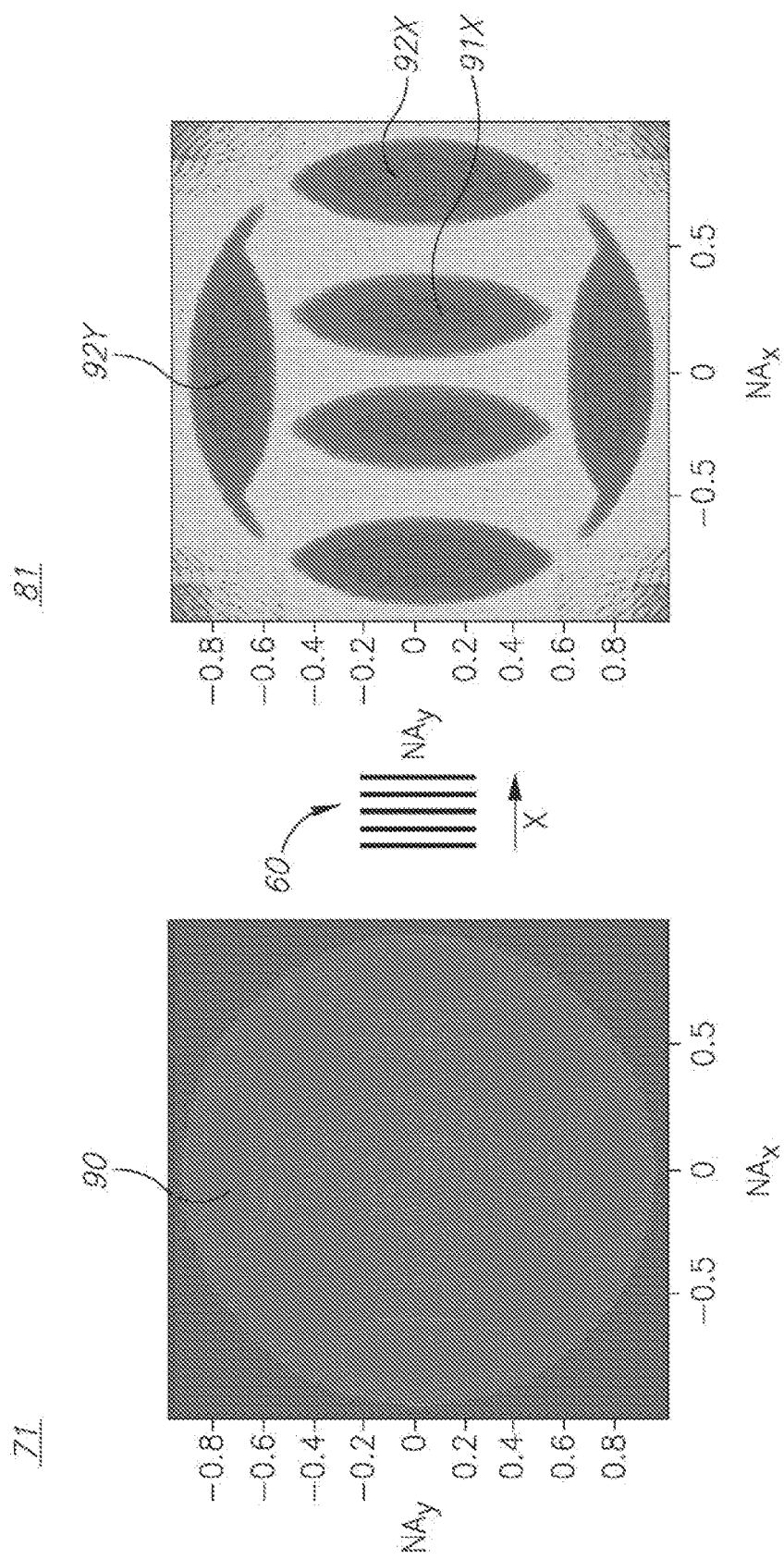
FIG. 1 is a high level schematic illustration of prior art scatterometry illumination.

Prior to the detailed description being set forth, it may be helpful to set forth definitions of certain terms that will be used hereinafter.

The term "periodic structure" as used in this application refers to any kind of designed or produced structure in at least one layer which exhibits some periodicity. The periodicity is characterized by its pitch, namely its spatial frequency. The term "measurement direction" as used in this application refers to the direction along which the periodic structure is periodic. For example, the measurement direction of a grating as the periodic structure is perpendicular to the elements of the grating.

The term "opposite illumination beams" as used in this application refers to illumination beams which are arranged symmetrically about the point in the illumination pupil associated with the normal to the target surface.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

It is noted that, in the present application, all images are shown with pupil plane relative coordinates $NA_x$, $NA_y$, defined with respect to the numerical aperture (NA) of the pupil. However, the invention disclosed below is not limited to NA=1 applications, for example using some immersion objective allows NA=1.5 or higher NAs. While the notation and figures describe non-limiting examples of illumination systems with NA=1, the disclosure further comprises modification that are applicable to higher NA values.

Scatterometry measurement systems, illumination configurations and respective methods are provided, which comprise illumination beams that have vertical projections on a target plane comprising both a parallel component and a perpendicular component, with respect to a target measurement direction. The illumination beams propagate at an angle to the plane defined by the measurement direction and a normal to the targets surface and generate diffraction images which are off-center at the imaging pupil plane. The eccentric diffraction images are spatially arranged to avoid overlaps and to correspond to measurement requirements such as spot sizes, number of required diffraction orders and so forth. The illumination beams may be implemented using illumination pupil masks, which provide a simple way to increase scatterometry measurements throughput. In certain embodiments, the illumination beams may be formed in a different way, for example by directing respective laser beams at the field plane, and not necessarily by applying a pupil mask.

Figure 2:
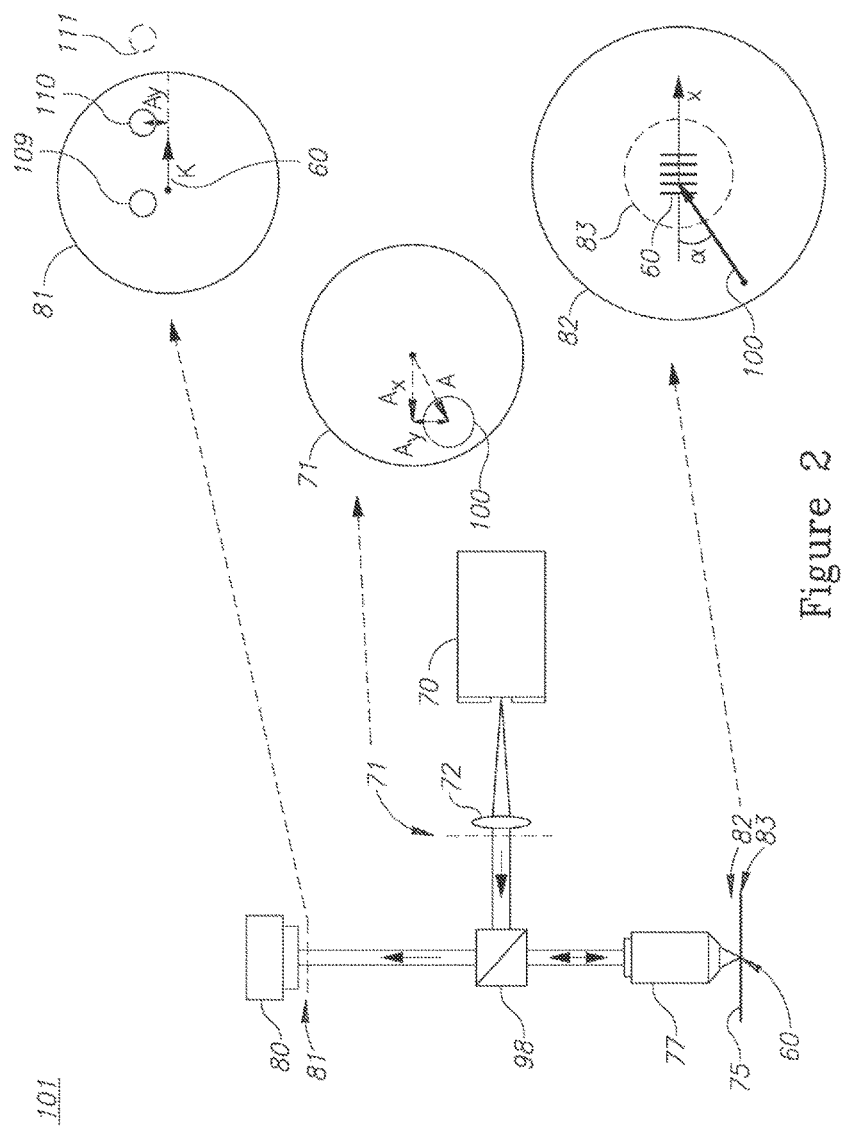
FIG. 2 is a high level schematic illustration of a scatterometry measurement system and illumination beams, according to an embodiment of the invention.

FIG. 2 is a high level schematic illustration of a scatterometry measurement system 101 and illumination beams 100, according to some embodiments of the invention. Scatterometry measurement system 101 comprises at least one illumination beam 100. A vertical projection of illumination beam 100 on a target plane comprises both a parallel component and a perpendicular component, with respect to a target measurement direction (x). The illumination propagation direction is out of the plane (by angle α) defined by the target's grating direction and the normal to the target's surface, or, stated differently, the plane established by the target measurement direction and the normal to the target surface.

FIG. 2 illustrates measurement system 101, having illumination source 70, lens 72 with illumination pupil plane 71, beam splitter 98, objective 77, wafer 75 with target 60 at field plane 83 with a plane 82 slightly above target 60 used to illustrate beams 100's illumination angle and detector 80 with respective image pupil plane 81 (the illustration of detector 80 at the pupil plane is non-limiting, but commonly used when capturing scatterometry images). FIG. 2 illustrates an illumination mask at illumination pupil plane 71 that creates illumination beam 100, a top view of the illumination of target 60 by beam 100, and an image pupil plane view of resulting diffraction images, in a non-limiting example diffraction images 109, 110, 111 of orders −1, 0, +1 (the latter being outside the pupil numerical aperture) created at image pupil plane 81 by the incidence of beam 100 on target 60. It is noted that illustrated input pupil images 71 may be understood as respective apodizer masks that determine the forms and positions of illumination beams 100. Form, sizes and exact positions of illumination beam windows are not limiting, and may be optimized with respect to specific requirements.

At illumination pupil plane 71, illumination beam(s) 100 is positioned off a target axis and off an axis perpendicular to the target axis, i.e., in the illustrated example, a distance $A_y$ off the horizontal measurement direction and a distance $A_x$ off the direction perpendicular to the measurement direction. Thus, illumination beam(s) 100 propagates at an angle α off a plane defined by the measurement direction (x) and a normal to target 60 (being essentially the system's optical axis). Angle α is defined between the vertical projection of illumination beam 100 on the target surface and the target's measurement direction. As a result, diffraction images 109, 110, 111 of target 60 at pupil plane 81 are off the target's measurement axis (designated at the pupil plane by k, originating from the pupil point associated with normal incidence at target 60) at a distance that corresponds, in terms of numerical aperture to $A_y$. The spread between the image orders correspond to the ratio λ/p between the illumination wavelength λ and the target pitch p, as discussed below.

In the following illustrations, illumination beams 100 are illustrated at illumination and imaging pupil planes 71, 81 (respectively) as circles which determine the angular distribution of illumination beams 100 on the target at field plane 82-83. It is noted that the form of beams 100 at the pupil planes is illustrated as circles is non-limiting, and actual beam forms at the pupil planes may be non-circular, e.g., elliptic, square, be a circle—torus intersection etc., according to specific designs for optimizing illumination and measurements. Different designs may be determined by considerations such as illumination intensity (i.e., area at the pupil plane which is occupied by the illumination beams), form with respect to the measurement direction, relation to illumination wavelengths and target pitches, beam generation considerations (e.g., producibility of pupil masks, or fiber optics) and so forth.

FIGS. 3A-3E are high level schematic illustrations of three exemplary illumination beam arrangements and resulting diffraction distributions, according to some embodiments of the invention. The figures schematically illustrate illumination patterns 71 and resulting diffraction images 81 for three exemplary types of targets 60, according to some embodiments of the invention. Neither the target types nor the illumination patterns are to be understood as limiting the invention, but rather as examples for illumination principles and system configuration principles. It is noted that, in the figures, the target measurement direction is represented at pupil plane 81 by arrow k, originating from the pupil point associated with normal incidence at target 60.

Figure 3A:
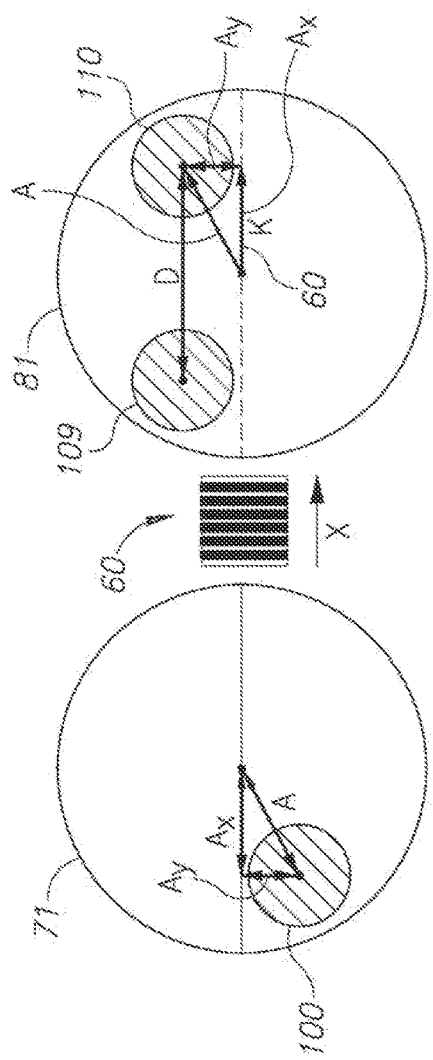
FIG. 3A is a high level schematic illustration of an exemplary illumination beam arrangement and the resulting diffraction distribution according to an embodiment of the invention.
Figure 3B:
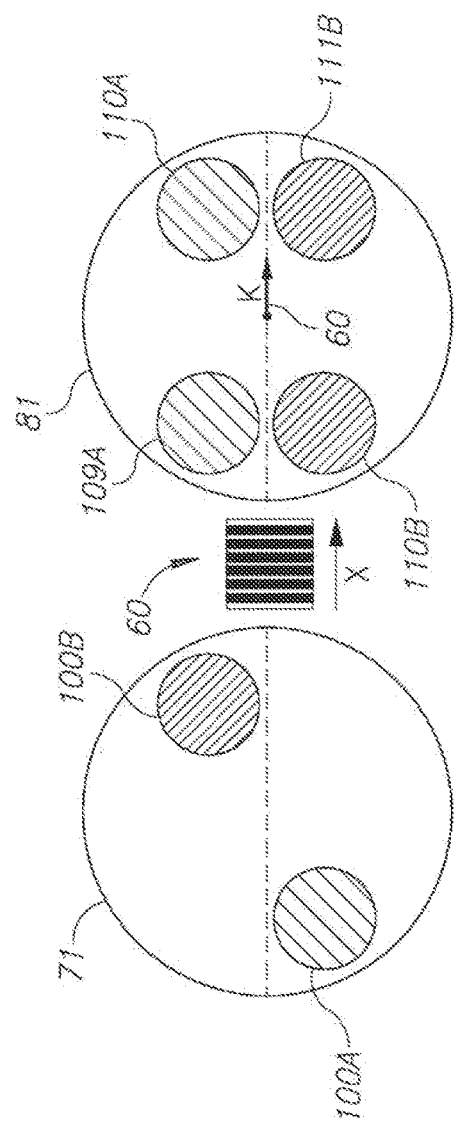
FIG. 3B is a high level schematic illustration of an exemplary illumination beam arrangement and the resulting diffraction distribution according to an embodiment of the invention.
Figure 3C:
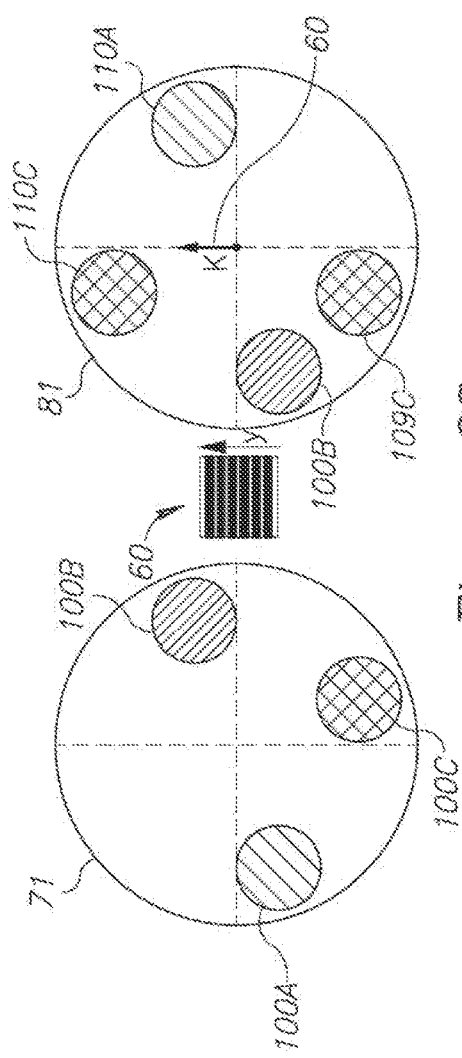
FIG. 3C is a high level schematic illustration of an exemplary illumination beam arrangement and the resulting diffraction distribution according to an embodiment of the invention.
Figure 3D:
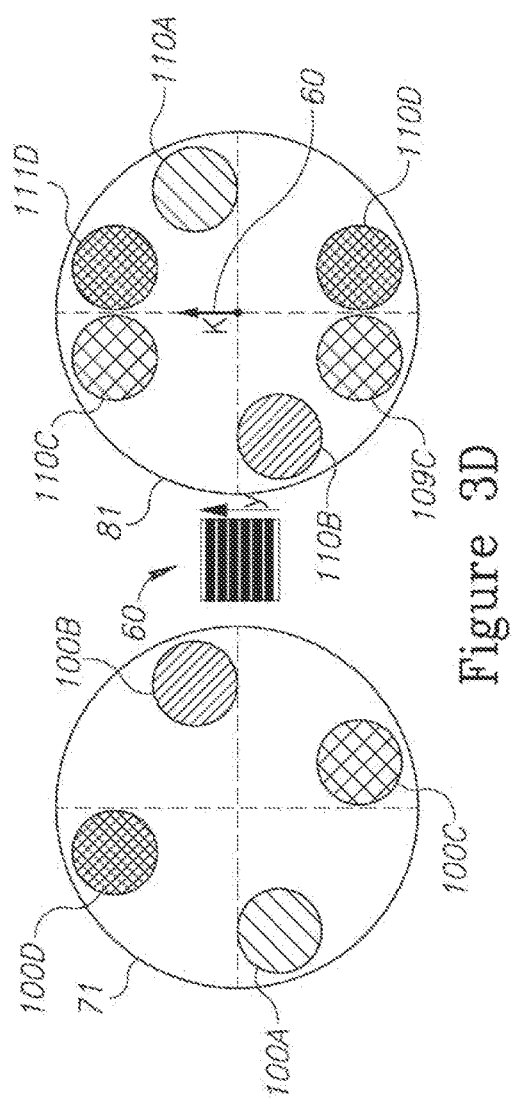
FIG. 3D is a high level schematic illustration of an exemplary illumination beam arrangement and the resulting diffraction distribution according to an embodiment of the invention.
Figure 3E:
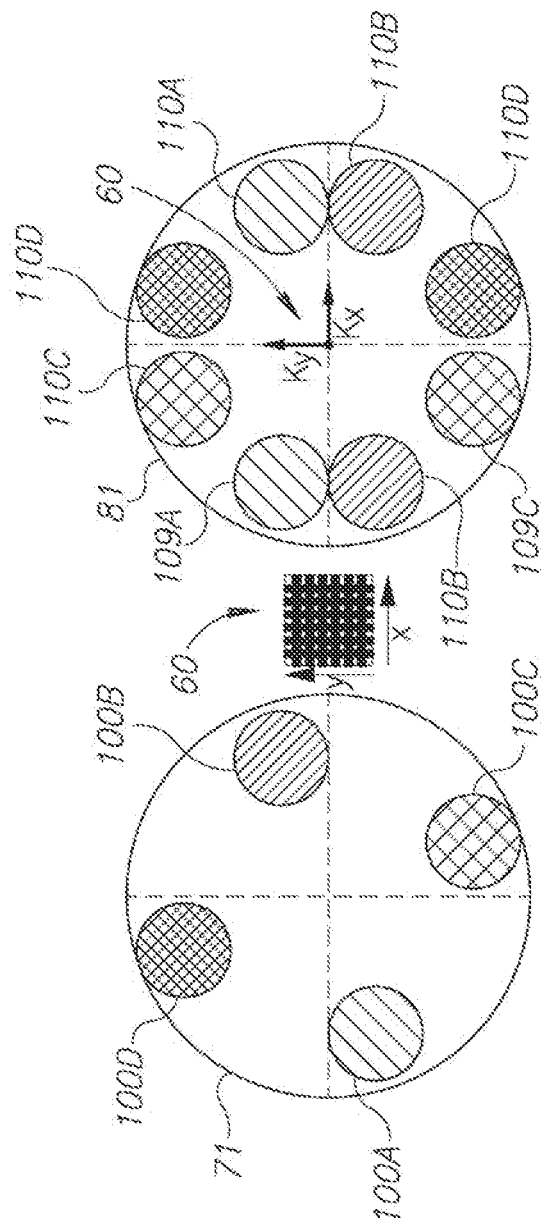
FIG. 3E is a high level schematic illustration of an exemplary illumination beam arrangement and the resulting diffraction distribution according to an embodiment of the invention.

FIGS. 3A and 3B schematically illustrate target 60 having a horizontal measurement axis (x) with a respective pair of illumination beams 100A, 100B (FIG. 3B) configured to enable scatterometry measurements of target 60. FIGS. 3C and 3D schematically illustrate target 60 having a perpendicular measurement axis (y) with an additional pair of illumination beams 100C, 100D configured to enable scatterometry measurements of target 60 along y axis as well. FIG. 3E schematically illustrates bi-dimensional target 60 having both horizontal measurement axis (x) and perpendicular measurement axis (y), and the respective two pairs of illumination beams 100A-D configured to enable scatterometry measurements of target 60 along both axes simultaneously.

FIG. 3A illustrates single beam 100 at an offset A from the pupil point associated with normal incidence at target 60, having offset $A_y$ from the x measurement direction and offset $A_x$ from the perpendicular direction thereto (y) at illumination pupil plane 71 and generating a zeroth order diffraction image 110 at image pupil plane 81, at a corresponding offset A (in numerical aperture coordinates) from the pupil point associated with normal incidence at target 60, having offset $A_y$ from the x measurement direction and offset $A_x$ from the perpendicular direction thereto (y), as well as a −1 diffraction order image 109 at a distance D proportional to λ/p and within imaging pupil plane 81. FIG. 3B schematically illustrates a pair of opposite illumination beams 100A, 100B (opposite with respect to target 60 and its measurement direction, i.e., illumination beams which are arranged symmetrically about the point in the illumination pupil associated with the normal to the target surface) at illumination pupil plane 71, each generating corresponding and non-overlapping target images of zeroth order 110A, 110B (respectively) and of first order (−1 order, 109A and +1 order 111B, respectively).

FIG. 3C illustrates, in addition to beams 100A, 100B for scatterometry measurements along the measurement direction x, a single beam 100C at an offset from target 60 along the measurement direction y at illumination pupil plane 71 and generating a zeroth order diffraction image 110C at image pupil plane 81, at a corresponding offset (in numerical aperture coordinates) from target 60, as well as a −1 diffraction order image 109C at a distance proportional to λ/p and within imaging pupil plane 81. FIG. 3D schematically illustrates two pairs of opposite illumination beams 100A, 100B (in the x direction) and 100C, 100D (opposite with respect to target 60 and its measurement direction), respectively, at illumination pupil plane 71. Beams 110A, 110B generate target images of zeroth order 110A, 110B at the x direction, while beams 100C, 100D generate corresponding and non-overlapping target images of zeroth order 110C, 110D and of first order 109C, 111D along the y direction. Beams 100A-100D may be arranged spatially to avoid or minimize overlapping of resulting images 110A-110D, 109C, 111D.

FIG. 3E schematically illustrates two pairs of opposite illumination beams 100A, 100B and 100C, 100D, respectively, illuminating target 60 having two measurement directions x, y. Beams 100A-100D are illustrated at illumination pupil plane 71, and the generated corresponding and non-overlapping target images are shown at image pupil plane 81 and comprise zeroth order images 110A, 110B and first order images 109A, 111B for the x direction pair of beams 100A, 100B and corresponding and non-overlapping target images of zeroth order 110C, 110D and of first order 109C, 111D for the y direction pair of beams 100C, 100D. Beams 100A-100D may be arranged spatially to avoid or minimize overlapping of resulting images 110A-110D, 109A, 111B, 109C, 111D. In certain embodiments, sizes and positions of illumination spots (determined e.g., by illumination pupil mask apertures) may be optimized to avoid overlapping of the diffracted orders in one dimension with the illumination nodes of a second dimension, for the whole range of diffraction angles.

While FIGS. 3D and 3E are examples for quadruple illumination, and while FIG. 3B is an example for dipole illumination, in certain embodiments, illumination beams may be configured to enable scatterometry measurements along respective three or more measurement directions. Single illumination beams 100 or pairs of illumination beams 100 may be configured to measure along each direction, and measurements from different beams may be combined to yield scatterometry measured at a given direction.

Advantageously, disclosed embodiments enable the use of angle resolved scatterometry overlay (SCOL) measurements with large value wavelength/pitch combinations, using either a single pupil mask for both x and y dimension or a single pupil mask for each dimension. Overlay offset measurement is implemented by an angle resolved scatterometry technology, such as the 4-cell measurement technology of the Archer500LCM. There, a "grating on grating" target diffracts a specific illumination, whereupon a resulting diffracted light is collected and analyzed. The diffraction angle is proportional to the illumination wavelength and inversely proportional to the grating's pitch. The use of a longer illumination wavelength and a smaller pitch grating, which are enabled in the disclosure, results in achieving larger diffraction angles. In an embodiment of the illumination method, the overlap between diffracted orders is inherently absent, thus achieving quadruple type illumination without its limitations (which were illustrated in FIG. 1). Similar to the quadruple illumination, the target may be illuminated with two illuminations per dimension (X,Y), each hitting the target at an illumination angle that is outside of the plane defined by the grating direction and the normal to the target's surface. In the pupil plane the corresponding spots are spatially distinct from the diffracted light. This may be implemented through the use of apertures in a mask in the pupil plane. The mask is opaque except for openings at positions which are spatially off the mask's center and off the target's measurement direction and the perpendicular direction thereto. The mask center corresponds to an on-face illumination of the target.

FIG. 4 is a simulated example for scatterometry measurements along the x axis, according to some embodiments of the invention. Two pairs of illumination beams 100A, 100B and 100C, 100D are illustrated at illumination pupil plane 71 and corresponding zeroth order images 110A-110D as well as first order images 109A, 111B are illustrated at image pupil plane 81 (similarly to FIG. 3B and to the y axis measurements illustrates in FIG. 3D). It is noted, that illumination beams 100A-D are asymmetrically (e.g., counterclockwise) rotated with respect to the prior art illumination illustrated on the left side of FIG. 1, and the resulting diffraction patterns avoid the spatial limitations imposed by prior art illumination beams, as neither do ±1 diffraction orders overlap zeroth order images, nor do +1 and −1 diffraction images of opposing illumination beams overlap.

Figure 5:
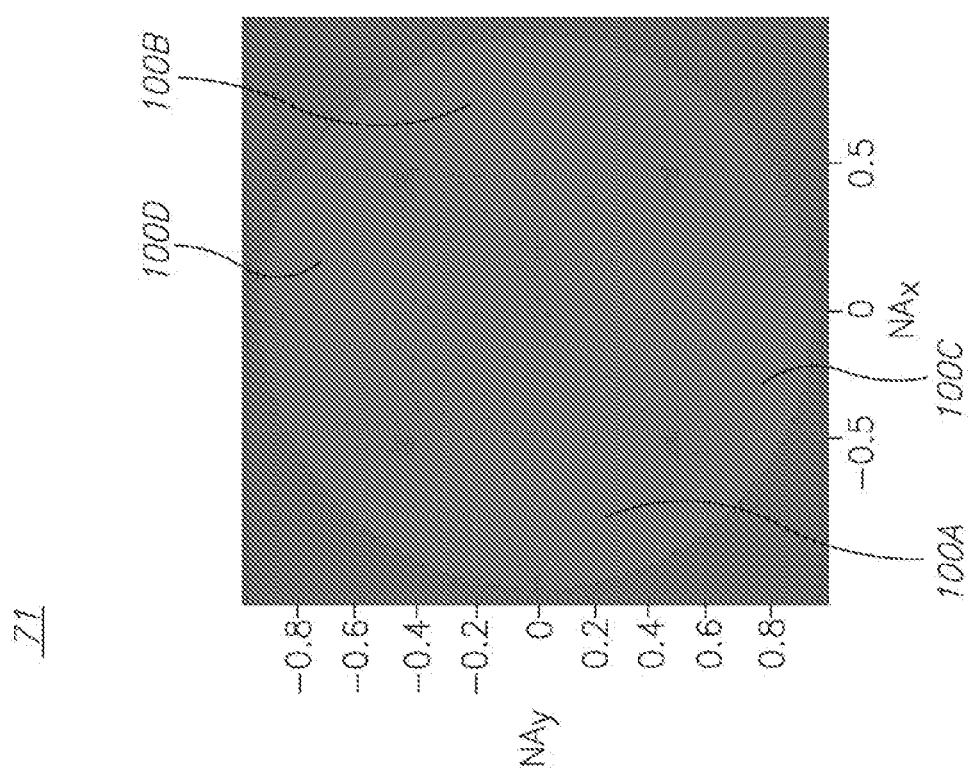
FIG. 5 is a simulated example for scatterometry measurements along the y axis according to some embodiments of the invention.

FIG. 5 is a simulated example for scatterometry measurements along the y axis, according to some embodiments of the invention. In FIG. 5 illumination beams 100A-D are not distributed evenly on the periphery of illumination pupil plane 71 and yet they form non-overlapping zeroth and ±1 diffraction order images of targets along the x and y axes. FIG. 5 schematically illustrates an alternate method of construction, comprising a similar pattern of illumination which may be achieved by illuminating target 60 from different directions directly, i.e., not through the use of illumination pupil apodization. Such a direct implementation may be realized by an arrangement of mirrors and beam splitters. Alternatively, variations of the configurations of illumination beams may be derived by changing the exact positions of the beams. For example, any pair of illumination beams may be mirrored with respect to a central axis. FIG. 5 schematically exemplifies such an example, in which beams 100C, 100B are relocated (or reflected) with respect to the y axis of the pupil plane. Similarly, beams 100A, 100B may be reflected with respect to the x axis. Moreover, the exact beams positions and beam sizes may be modified, as exemplified below. Thus, any particular illumination pattern in the present disclosure is understood as representing a family of similar illumination patterns which may be derived from each other by such transformations.

FIGS. 6A-6C are high level schematic illustrations of illumination beam arrangements which allow scatterometry measurements at multiple wavelengths, according to some embodiments of the invention. Using illumination beams 100A-100D illustrated in FIG. 4 (left) as a non-limiting example, FIGS. 6A-6C schematically illustrate the resulting diffraction images for target 60 at measurement direction x, for two illumination wavelengths $\lambda_1 > \lambda_2$, e.g., $\lambda_1 = 800$ nm, $\lambda_2 = 250$ nm. FIG. 6A roughly corresponds to FIG. 4 (right) in the configuration of diffraction images 110A-D, 109A and 111B. In case $\lambda_1$ is the longest wavelength to be measured by system 101, target pitch p may be selected to accommodate diffraction images 109A, 110A and 110B, 111B within the width of the image pupil NA (see distance $D = \lambda_1/p$). At shorter wavelengths $\lambda_2$, as illustrated in FIG. 6B, diffraction images 109A, 110A and 110B, 111B are pairwise closer to each other, and optionally even illumination beams 100C, 100D, intended to measure diffraction along the y direction, may be used to achieve additional ±1 order diffraction images 109C (−1), 111D (+1) and possibly even parts of 111C (+1), 109D (−1). Illumination beams 100 and possible apodization thereof may be configured to spatially accommodate the diffraction images within the NA of the pupil plane. In certain embodiments, the apodization may be carried out with respect to the amplitude and/or to the phase of the beam, and may be configured to reduce overlap between diffraction images of the beams while minimizing a size of respective illumination spots on the target.

FIG. 6C schematically illustrates, that for short wavelengths $\lambda_2$, higher diffraction orders may be accommodated within the numerical aperture, e.g., ±2 diffraction orders such as 112B, 108A. In certain embodiments, illumination beams 100 may be positioned to yield at least one measurable first order diffraction image of target 60 within a specified range of wavelength to pitch ratios. In certain embodiments, illumination beams 100 may be positioned to yield at least one measurable second order diffraction image of target 60. In certain embodiments, target parameters (e.g., pitch) and illumination parameters (e.g., wavelength, extent and angle of beams 100) may be configured to accommodate a specified number of diffraction orders of each beam within imaging pupil plane 81. In certain embodiments, second (or higher) order diffraction images may be used to derive additional accuracy data (beyond overlay, e.g., relating to distortions of the periodic structures, such as gratings), and thus comparing diffraction images of different orders may be used to isolate specific sources of inaccuracy and specific geometric characteristics of the targets.

In certain embodiments, system 101 and the disclosed illumination designs may be implemented for scatterometry overlay measurement of layers made from polysilicon, with longer wavelengths used to probe the wafer beneath the polysilicon layer. Hence, wavelength flexible embodiments may be used to derive scatterometry measurements of different wafer layers.

Advantageously, spot size and positions may be chosen to allow full flexibility of wavelength/pitch combinations, by ensuring that at each resulting diffraction angle, no overlap is created between orders.

FIGS. 7A-7C are high level schematic illustrations of illumination beam arrangements which optimize scatterometry measurements at a given wavelength, according to some embodiments of the invention. System 101 may comprise a single pair of illumination beams 100A, 100B which are positioned to allow scatterometry measurements of target 60 along two measurement directions (e.g., x and y). In certain embodiments, the extent of beams 100A, 100B may be maximized within the numerical aperture of the image pupil to optimize measurement accuracy. FIG. 7A schematically illustrates illumination pupil 71 with two opposite beams 100A, 100B. FIG. 7B, 7C schematically illustrates scatterometry measurements of targets 60A, 60B, having measurement directions x and y respectively. Respective image pupils 81A, 81B illustrate that each beam 100A, 100B contributes one zeroth order diffraction image 110A, 100B and one first order diffraction image 109A (−1), 111B (+1) respectively, in either measurement direction.

In certain embodiments, FIG. 7A illustrates a dipole type implementation for measurement in one dimension only (X or Y), comprising of two nodes (left, right for X measurements and top, bottom for Y measurements). In this implementation, the working principle is the same, however, the apertures can be made bigger (as they are not constrained by the illuminations of the other dimension). The bigger aperture in the pupil plane will result in smaller spot size on the target, allowing the use of smaller targets, which is desirable. In certain embodiments, the size of the individual apertures may be maximized to yield minimal spot sizes on target 60, while avoiding overlapping among the diffraction orders.

Advantageously, large illumination beams 100A, 100B at pupil plane 71, allow the largest possible illumination NA and thereby the smallest possible illumination spot on target (minimizes signal contamination from target periphery). Furthermore, such beams are compatible with objective lenses that obscure the center of the pupil (see FIG. 8B below) and the same dipole apertures can be used for both X and Y targets (FIGS. 7B, 7C).

FIGS. 8A, 8B are high level schematic illustrations of wavelength-adaptable illumination and wavelength-optimized illumination, respectively, according to some embodiments of the invention. FIG. 8A schematically illustrates measurements with an exemplary single pair of illumination beams 100A, 100B along the x direction (as in FIG. 3A for FIG. 8A and as in FIG. 7A for FIG. 8B), which may be carried out at a range of wavelengths $\lambda_2$ (e.g., 700 nm) to $\lambda_1$ (e.g., 260 nm), with respect to a target pitch of 600 nm. At different wavelengths, first order diffraction patterns 109A (−1) and 111B (+1) change position without overlapping. FIGS. 8A, 8B further illustrate an obscuring disc 105 configured to remove central illumination, a feature which in prior art intervenes with measurements, but is acceptable in the disclosed embodiments. For example, obscuring disc 105 may be implemented using optical blocks in certain catadioptric (reflective and refractive) objective lenses. The range of wavelengths (and/or of target pitches) that is accommodated within pupil image 81 corresponds to the spatial range of distances between the zeroth and first diffraction orders, namely the range $\lambda_2/p$ to $\lambda_1/p$.

Illumination beams 100A, 100B may be positioned symmetrically about the center of the pupil, and the overlay signal may be derived from the intensity difference between −1 diffraction order from one illumination beam (e.g., 109A) and +1 diffraction order from the other illumination beam (e.g., 111B). The distance in the pupil between ±1 diffraction orders and the 0 order depends on wavelength and target pitch. Target pitch may be selected so that ±1 diffraction orders do not overlap 0 orders at the shortest intended measurement wavelength and fall within the collection aperture at the longest intended measurement wavelength.

Illumination beams 100 may be positioned in the pupil so that the direction of diffraction does not cause the diffracted orders to overlap the other beam or a central obscuration in the pupil (should one exist). Advantageously, such a configuration allows the greatest range of illumination wavelengths to be used for a given target pitch and is compatible with objective lenses that obscure the center of the pupil (105). Furthermore, illumination beams may be positioned uniquely for each measurement wavelength so that higher diffraction orders are not partially truncated by the aperture (truncation introduces stray light into the measurement).

FIG. 8B schematically illustrates measurements which are carried out for a given $\lambda/p$ ratio and maximize pupil area utilization by illumination beam pair having illumination beams 100A, 100B. For example, for a given $\lambda/p$ ratio of 0.74, pitches in the range 351-946 nm may be used at respective wavelengths of 260-700 nm to optimize pupil utilization, even with obscured center 105. Illumination beams 100A, 100B may be positioned symmetrically about the center of the pupil in opposing quadrants. The overlay signal may be derived from intensity difference between −1 diffraction order from one illumination beam (109A) and +1 diffraction order from the other illumination beam (111B). As the distance in pupil between ±1 diffraction orders and 0 orders depends on wavelength and target pitch, target pitch may be selected so that ±1 diffraction orders do not overlap 0 orders at the intended measurement wavelength and are not truncated by the collection aperture.

Figure 9A:
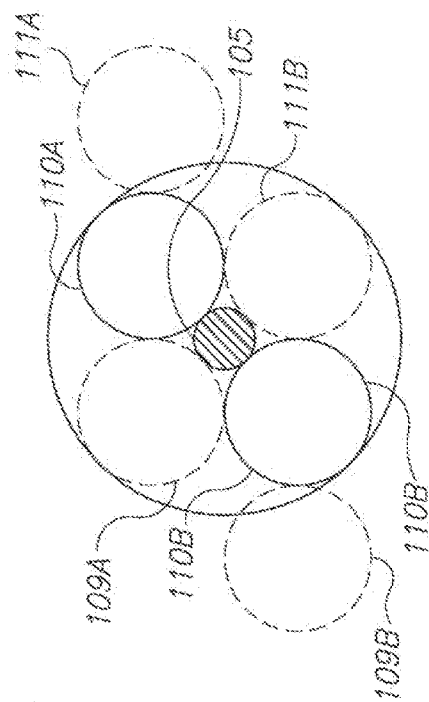
FIG. 9A is a high level schematic illustration of a wavelength-adaptable illumination pattern according to an embodiment of the invention.
Figure 9B:
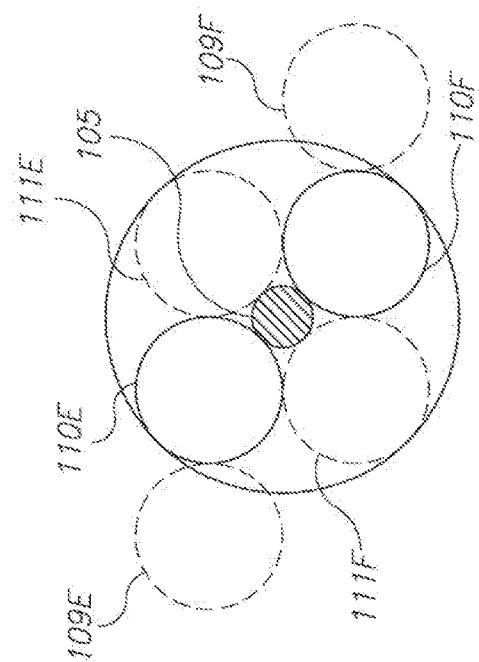
FIG. 9B is a high level schematic illustration of a wavelength-adaptable illumination pattern according to an embodiment of the invention.
Figure 10A:
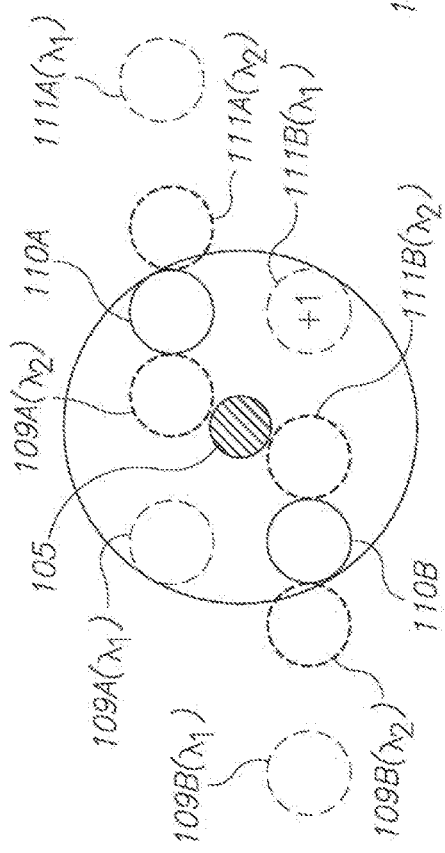
FIG. 10A is a high level schematic illustration of a wavelength-optimized illumination pattern according to an embodiment of the invention.
Figure 10B:
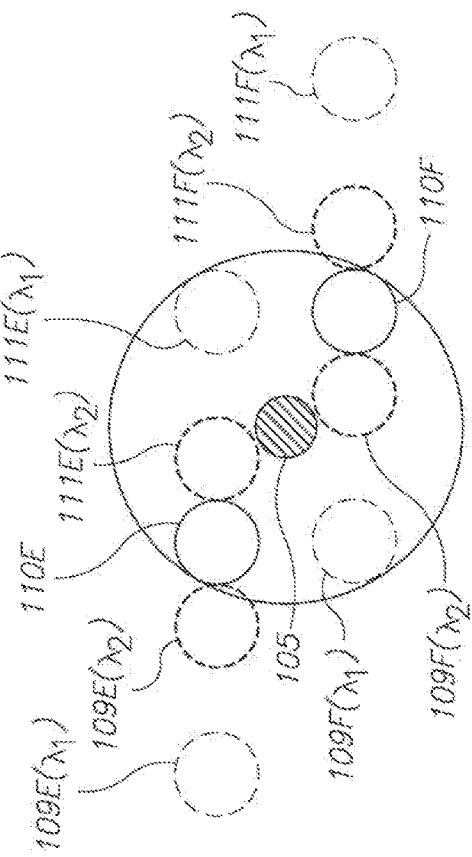
FIG. 10B is a high level schematic illustration of a wavelength-optimized illumination pattern according to an embodiment of the invention.

FIGS. 9A and 9B are high level schematic illustrations of wavelength-adaptable illumination patterns, according to some embodiments of the invention. FIGS. 10A and 10B are high level schematic illustrations of wavelength-optimized illumination patterns, respectively, according to some embodiments of the invention.

FIG. 9A schematically illustrates an illumination similar to FIG. 8A. FIG. 9B schematically illustrates a mirrored illumination of FIG. 9A. The diffraction images of the mirrored illumination beams are denoted by 110E and 110F (zeroth order) and 109E, 111E and 109F, 111F for ±1 orders of each beam, respectively.

FIG. 10A schematically illustrates an illumination similar to FIG. 8B. FIG. 10B schematically illustrates a mirrored illumination of FIG. 10A. The diffraction images of the mirrored illumination beams are denoted by 110E and 110F (zeroth order) and 109E, 111E and 109F, 111F for ±1 orders of each beam, respectively.

In either case shown in FIG. 9A, 9B or 10A, 10B, full symmetry in the measurements may be achieved by capturing two separate pupil images, each with a dipole configuration (i.e., pairwise arrangement of the illumination beams) that is the mirror of the other. The overlay signal may be derived from the difference between the sums of the two +1 orders and the two −1 orders. Full symmetry may be desirable for minimizing errors due to asymmetry such as polarization rotation.

In any of the disclosed embodiments, any of the illumination beams may be apodized to optimize the spatial distribution of the respective diffraction images. Illumination beam apodization may be configured to reduce overlap between diffraction images of the beams. In any of the embodiments, illumination beam patterns may be created using pupil plane patterned illumination masks according to the disclosed patterns, i.e., configured to determine a position of illumination beam(s) 100 at pupil plane 71, and potentially including appropriate apodization of the illumination beams. Diffraction images of beams 100 as well as scatterometry measurements comprising the diffraction images are likewise part of the present disclosure, as are scatterometry measurements comprising at least one diffraction image positioned in a pupil plane off a target axis and off an axis perpendicular to the target axis.

Comparing FIGS. 9A and 10A, it is noted that the angular extent of illumination beams 100 (corresponding to the angular extent of illumination beams on target 60 at field plane 83) may be modified to balance illumination intensity and range of measurable $\lambda/p$ ratios. For example, the diameter of the pupil area occupied by each illumination beam 100 may range between 0.2 NA or lower (FIG. 9A) and 0.4 NA or higher (FIG. 10A). The shape of illumination beam 100 at the pupil plane may be modified to increase illumination, to enhance measurement sensitivity to given target characteristics and with respect to production and measurement considerations.

Figure 11:
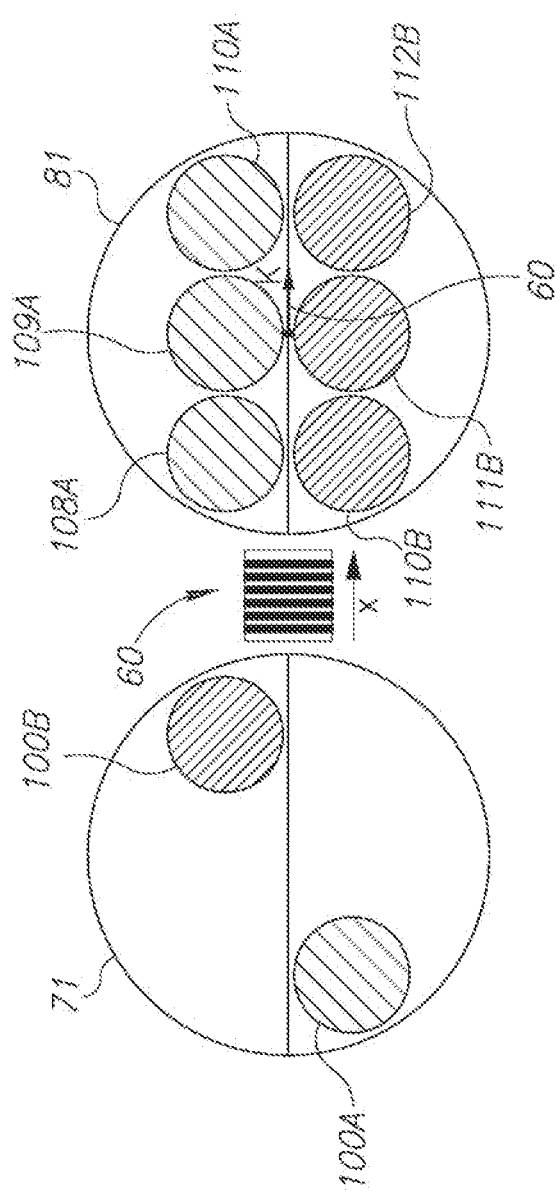
FIG. 11 is a high level schematic illustration of the accommodation of several diffraction orders within imaging pupil plane, according to some embodiments of the invention; and, FIG. 12 is a high level schematic flowchart illustrating a method according to an embodiment of the invention.

FIG. 11 is a high level schematic illustration of the accommodation of several diffraction orders within imaging pupil plane 81, according to some embodiments of the invention. As in the figures presented above, input pupil image 71 may be understood as an apodizer mask that determines the forms and positions of illumination beams 100. Target parameters (e.g., pitch) and illumination parameters (e.g., wavelength, extent and angle of beams 100) may be configured to accommodate a specified number of diffraction orders of each beam within the NA of imaging pupil plane 81. In the illustrated example, target and illumination parameters are configured to include within imaging pupil plane 81 zeroth, first and second order diffraction images of the illumination beams, specifically—110A zeroth order, 109A first (−1) order, 108A second (−2) order diffraction images of beam 100A; 110B zeroth order, 111B first (+1) order, 112B second (+2) order diffraction images of beam 100B). In certain embodiments, a larger number of diffraction image orders may be configured to be within the NA of imaging pupil plane 81 and/or two or more diffraction orders of images in different measurement directions may be accommodated into the NA of imaging pupil plane 81.

In certain embodiments, accommodating diffraction orders beyond the first order in the NA of the imaging pupil improves the accuracy of overlay scatterometry measurements by optimizing target shift (designed overlay $f_0$) selection. While current scatterometry overlay (SCOL) target designs are optimized for zero and first order SCOL, the present disclosure further comprises SCOL targets which are optimized for higher order diffraction images, which, through the disclosed illumination patterns, improves the accuracy of the measurements. For example, the disclosed invention enables to distinguish and quantify process variations other than overlay, which represent themselves as overlay errors when using zeroth and first order images. For example, the disclosed invention enables to measure target aberrations resulting from targets which are not design-rules compatible, or have pitches larger than typical devices pitches.

FIG. 12 is a high level schematic flowchart illustrating method 200 according to some embodiments of the invention. Method 200 may comprise any of the following stages, and includes designing of the illumination patterns, controlling the actual illumination, and measuring resulting scatterometry images.

Method 200 may comprise illuminating a scatterometry target with illumination beam(s) having both parallel and perpendicular components of their vertical projection on the target plane (stage 210). Stated differently, method 200 may comprise configuring the illumination propagation direction to be out of a plane defined by the target's measurement direction and a normal to the target (stage 212). Method 200 may further comprise illuminating the target with one or more pairs of opposite illumination beams (stage 220).

Method 200 may comprise positioning the illumination beams to allow scatterometry measurements of the target along two measurement directions (stage 230). Method 200 may comprise using one, two or more pairs of opposite illumination beams. Method 200 may comprise any of: positioning the illumination beams in a pupil plane to be off a target axis and off an axis perpendicular to the target axis (stage 240), arranging the illumination beam(s) at a periphery of the pupil plane (stage 250) and configuring a pupil illumination mask to determine a position of the illumination beam(s) at the pupil plane (stage 260).

In certain embodiments, method 200 may comprise positioning the illumination beam(s) to yield measurable first order diffraction image(s) of the target within a specified range of wavelength to pitch ratios (stage 270) and possibly positioning the illumination beam(s) to yield measurable second order diffraction image(s) of the target (stage 280). Method 200 may further comprise configuring target and illumination parameters to accommodate a specified number of diffraction orders of each beam within the imaging pupil plane (stage 282).

Method 200 may further comprise configuring illumination beams' apodization to reduce overlap between diffraction images of the beams (stage 290). In certain embodiments, the apodization may be with respect to the amplitude and/or the phase of the beams, and method 200 may further comprise configuring the apodization to reduce overlap between diffraction images of the beams while minimizing a size of respective illumination spots on the target (stage 295).

Method 200 may comprise measuring diffraction image(s) of the respective illumination beam(s) diffracted off the target (stage 300).

In certain embodiments, method 200 may further comprise applying the illumination beams sequentially (stage 310) within a time frame used for measuring the resulting diffraction images. For example, in case of two illumination beams 100, a first beam (e.g., 100A) may be configured to illuminate target 60 during the first half of the time frame while a second beam (e.g., 100B) may be configured to illuminate target 60 during the second half of the time frame, without or with partial temporal overlap between illumination by beams 100A, 100B. In case of four illumination beams 100A-D, each beam may be allotted part of the measurement frame, or any of the beams may be coupled, forming e.g., one pair at a time or sequential beams of each pair used to illuminate target 60. The temporal configuration of the beams may be selected to remove any interference effects resulting from the interaction of the light from the two nodes on the detector. Cross-talk is the situation where light from one node somehow arrives at the region of interest of another node. In this implementation the cross-talk is the sum of separately time integrated intensities. For example, in certain embodiments, method 200 may further comprise capturing sequential diffraction images from each illumination beam (stage 315). Illumination beams in a pair may be switched to illuminate the target sequentially and not simultaneously, thereby cancelling any interference between the respective illumination sources and diffracted images. For example, one illumination beam may be switched on, the diffraction orders (e.g., some of ±1, ±2, etc.) resulting from this beam may be captured by the detector, then this beam may be switched off and the other illumination beam of the pair may be switched on to capture the diffraction orders generated by it. Any order of switching illumination beams in a specified configuration may be used. The detector may operate continuously, detecting diffraction images resulting from all individual illumination beams. Clearly, sequential illumination may also be compared with simultaneous illumination. Illumination beams may also be applied pairwise, e.g., along different measurement directions.

In certain embodiments, method 200 may further comprise configuring at least one of the illumination beams to be incoherent (stage 320). Incoherent illumination may also be utilized to make the cross-talk equal the sum of separately time integrated intensities.

Certain embodiments further comprise scatterometry systems and modules implementing any stage of method 200, respective illumination masks as well as diffraction images and scatterometry measurements derived by method 200.

Advantageously, the disclosed invention enables measurements with longer wavelengths, which allow probing of semiconductor layers that were previously inaccessible. The disclosed invention further enables measurement with smaller pitch gratings, which are advantageous as their critical dimension is closer to the critical dimension of other elements on the wafer, thus reducing systemic errors. The disclosed invention further enables measurement with a larger range of wavelengths with a single method and/or implementation, which allows for operational flexibility, as one illumination pattern is used for different layers that are accessible to different wavelengths. Finally, the disclosed invention enables measurement with a larger range of pitch gratings which allows for operational flexibility, as one illumination pattern is used for different targets.

In certain embodiments, beams 100 have a smaller spot size, as compared to the previously demonstrated symmetric quadruple (compare e.g., FIG. 4 with FIG. 1). The smaller spot size allows for smaller targets. Alternatively, the smaller spot size for targets of the same size increases performance as target edge effects are reduced. Alternatively, the smaller spot size for the same size target increases performance as the illumination spot can be scanned across a larger part of the target, whereupon the largest spatial average serves to decrease effects of target noise.

Parasitic grating is a secondary structure embedded in the target, which diffracts some of the illumination in an angle different than the diffraction angle resulting from the primary structure of the target. Segmentation of target grating bars may introduce additional signals or modify the signal resulting from the main target grating. Certain embodiments of the disclosed invention are less sensitive to parasitic grating.

Advantageously, the disclosure extends the use of current measurement technology and tools that implement it (like Archer500LCM) to enable the measurements of overlay in layers that are not accessible today, in certain embodiments merely by preparing new illumination pupil masks to replace the currently installed illumination pupil masks. The adaptation of algorithms and software is straightforward and is hence considered part of the present disclosure.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A scatterometry measurement system, comprising:
   a scatterometry target having at least two layers and at least two periodic structures in which each periodic structure in the at least two periodic structures is disposed at a different layer and has a pitch;
   a detector; and
   an illumination source arranged to illuminate the scatterometry target with a first illumination beam at a first illumination angle and a second illumination beam at a second illumination angle to generate at least one diffracted order from each of the first illumination beam and the second illumination beam located entirely within a width of a numerical aperture of an imaging pupil plane, wherein at least one of the first illumination angle or the second illumination angle is outside of a plane defined by a grating direction and a normal to the scatterometry target such that the diffraction orders withinthe imaging pupil plane have a non-overlapping distribution.

2. The scatterometry measurement system of claim 1, wherein the illumination source is further arranged to illuminate the scatterometry target with a third illumination beam at a third illumination angle and a fourth illumination beam at a fourth illumination angle to generate at least one diffracted order from each of the third illumination beam and the fourth illumination beam located entirely within the width of the numerical aperture of the imaging pupil plane, wherein at least one of the third illumination angle or the fourth illumination angle is outside of the plane defined by the grating direction and the normal to the scatterometry target such that the diffraction orders within the imaging pupil plane have a non-overlapping distribution.

3. The scatterometry measurement system of claim 2, wherein the illumination source is arranged to transmit the third and fourth illumination beams through an illumination pupil plane located between the illumination source and the scatterometry target; and the imaging pupil plane is located between the scatterometry target and the detector.

4. The scatterometry measurement system of claim 2, wherein the scatterometry target includes a grating, wherein a target measurement direction is defined as being perpendicular to elements of the grating, wherein the third and fourth illumination beams include respective components parallel to the target measurement direction and respective components perpendicular to the target measurement direction.

5. The scatterometry measurement system of claim 2, wherein the illumination source is arranged to generate on the imaging pupil plane:
   second and third zero order diffraction images, respective entireties of which are located within the width of the numerical aperture of the imaging pupil plane; and
   second and third first order diffraction images, respective entireties of which are located within the width of the numerical aperture of the imaging pupil plane.

6. The scatterometry measurement system of claim 1, wherein the first illumination beam and the second illumination beam are positioned to allow scatterometry measurements of the scatterometry target along two measurement directions.

7. The scatterometry measurement system of claim 1, wherein the illumination source is arranged to transmit the first illumination beam through an illumination pupil plane located between the illumination source and the scatterometry target.

8. The scatterometry measurement system of claim 1, wherein the imaging pupil plane is located between the scatterometry target and the detector.

9. The scatterometry measurement system of claim 1, wherein the scatterometry target includes a grating, wherein a target measurement direction is defined as being perpendicular to elements of the grating, wherein the first illumination beam includes a component parallel to the target measurement direction and a component perpendicular to the target measurement direction.

10. The scatterometry measurement system of claim 1, wherein the illumination source is arranged to transmit the second illumination beam through an illumination pupil plane located between the illumination source and the scatterometry target, wherein the imaging pupil plane is located between the scatterometry target and the detector.

11. The scatterometry measurement system of claim 1, wherein the scatterometry target includes a grating, wherein a target measurement direction is defined as being perpendicular to elements of the grating, wherein the second illumination beam includes a component parallel to the target measurement direction and a component perpendicular to the target measurement direction.

12. The scatterometry measurement system of claim 1, wherein the illumination source is arranged to generate on the imaging pupil plane:
   a second zero order diffraction image, an entirety of which is located within the width of the numerical aperture of the imaging pupil plane; and
   a second first order diffraction image, an entirety of which is located within the width of the numerical aperture of the imaging pupil plane.

13. The system of claim 1, wherein the first illumination beam includes a first wavelength, wherein the second illumination beam includes a second wavelength different than the first wavelength.

14. The system of claim 13, wherein the scatterometry target diffracts the first illumination beam at a first diffraction angle proportional to the first wavelength and inversely proportional to the pitch, wherein the scatterometry target diffracts the second illumination beam at a second diffraction angle proportional to the second wavelength and inversely proportional to the pitch.

15. The system of claim 1, wherein the at least one diffracted order from each of the first illumination beam and the second illumination beam comprises:
   at least one of a 0-order diffraction beam, a ±1-order diffraction beam, or a 2-order diffraction beam.

16. A method comprising the step of:
   transmitting, from an illumination source, a first illumination beam and a second illumination beam; and
   illuminating a scatterometry target having at least two layers and at least two periodic structures in which each periodic structure in the at leasttwo periodic structures is disposed at a different layer with the first illumination beam at a first illumination angle and the second illumination beam at a second angle such that the scatterometry target diffracts the first illumination beam and the second illumination beam to generate at least one diffracted order from each of the first illumination beam and the second illumination beam located entirely within a width of a numerical aperture of an imaging pupil plane, wherein at least one of the first illumination angle or the second illumination angle is outside of a plane defined by the grating direction and a normal to the scatterometry target such that the diffraction orders within the imaging pupil plane have a non-overlapping distribution.

17. The method of claim 16, further comprising:
   transmitting, from the illumination source, a third illumination beam and a fourth illumination beam illuminating the scatterometry target with the third illumination beam at a third illumination angle and the fourth illumination beam at a fourth illumination angle to generate at least one diffracted order from each of the third illumination beam and the fourth illumination beam located entirely within the width of the numerical aperture of the imaging pupil plane, wherein at least one of the third illumination angle or the fourth illumination angle is outside of the plane defined by the grating direction and the normal to the scatterometry target such that the diffraction orders within the imaging pupil plane have a non-overlapping distribution.

18. The method of claim 17, wherein transmitting the third and fourth illumination beams through an illumination pupil plane located between the illumination source and the scatterometry target, wherein the fourth illumination beam is opposite the third illumination beam in the illumination pupil plane, wherein the imaging pupil plane is located between the scatterometry target and the detector.

19. The method of claim 17, wherein the scatterometry target includes a grating, wherein a target measurement direction is defined as being perpendicular to elements of the grating, wherein the third and fourth illumination beams include respective components parallel to the target measurement direction and respective components perpendicular to the target measurement direction.

20. The method of claim 16, further comprising:
   positioning the first illumination beam and the second illumination beam to allow scatterometry measurements of the scatterometry target along two measurement directions.

21. The method of claim 16, wherein the first illumination beam and the second illumination beam are positioned in an illumination pupil plane off a target axis and off an axis perpendicular to the target axis, the method further comprising:
arranging the at least one illumination beam at a periphery of the illumination pupil plane.

22. The method of claim 21, further comprising:
configuring a pupil illumination mask to determine a position of the at least one illumination beam at the illumination pupil plane.

23. The method of claim 16, further comprising:
positioning the first illumination beam and the second illumination beam to yield at least one measurable first order diffraction image of the scatterometry target within a specified range of wavelength to pitch ratios.

24. The method of claim 16, further comprising:
positioning the first illumination beam and the second illumination beam to yield at least one measurable second order diffraction image of the scatterometry target.

25. The method of claim 24, further comprising:
configuring target and illumination parameters to accommodate a specified number of diffraction orders of the first illumination beam and the second illumination beam within the imaging pupil plane.

26. The method of claim 16, wherein the first illumination beam and the second illumination beam comprise apodized beams, the method further comprising:
configuring an apodization of the apodized beams to reduce overlap between diffraction images of the apodized beams.

27. The method of claim 26, wherein the apodization is with respect to at least one of amplitude and phase, the method further comprising:
configuring the apodization to reduce overlap between diffraction images of the apodized beams while minimizing a size of respective illumination spots on the scatterometry target.

28. The method of claim 16, further comprising:
capturing sequential diffraction images from the first illumination beam and the second illumination beam.

29. The method of claim 16, further comprising:
measuring at least one diffraction image of at least one of the first illumination beam or the second illumination beam diffracted off the scatterometry target.

30. The method of claim 29, further comprising:
applying the first illumination beam and the second illumination beam sequentially within a measurement time frame.

31. The method of claim 29, further comprising:
configuring at least one of the first illumination beam or the second illumination beam to be incoherent.

32. The method of claim 16, further comprising:
transmitting, from the illumination source, the first illumination beam through an illumination pupil plane located between the illumination source and the scatterometry target, wherein the imaging pupil plane is located between the scatterometry target and the detector.

33. The method of claim 16, wherein the scatterometry target includes a grating, wherein a target measurement direction is defined as being perpendicular to elements of the grating, wherein the first illumination beam includes a component parallel to the target measurement direction and a component perpendicular to the target measurement direction.

34. The method of claim 16, further comprising:
transmitting the first illumination beam at a first wavelength;
locating a first diffracted order from the first illumination beam at a first position within the width of the numerical aperture of the imaging pupil plane;
transmitting the first illumination beam at a second wavelength different from the first wavelength; and
locating the first diffracted order from the first illumination beam at a second position within the width of the numerical aperture of the imaging pupil plane, the second position different from the first position.

35. The method of claim 16, further comprising:
transmitting the second illumination beam through an illumination pupil plane located between the illumination source and the scatterometry target, wherein the imaging pupil plane is located between the scatterometry target and the detector.

36. The method of claim 16, wherein the scatterometry target includes a grating, wherein a target measurement direction is defined as being perpendicular to elements of the grating, wherein the second illumination beam includes a component parallel to the target measurement direction and a component perpendicular to the target measurement direction.

* * * * *